(12) United States Patent
McDevitt et al.

(10) Patent No.: US 9,535,068 B2
(45) Date of Patent: Jan. 3, 2017

(54) ORAL CANCER POINT OF CARE DIAGNOSTICS

(75) Inventors: John T. McDevitt, Houston, TX (US); Nicolaos Christodoulides, Houston, TX (US); Pierre N. Floriano, Missouri City, TX (US); Martin Thornhill, Sheffield (GB); Spencer Redding, San Antonio, TX (US); Nadarajah Vigneswaran, Houston, TX (US); Craig Murdoch, Sheffield (GB); Paul Speight, Sheffield (GB)

(73) Assignee: William Marsh Rice University, Houston, TX (US)

( * ) Notice: Subject to any disclaimer, the term of this patent is extended or adjusted under 35 U.S.C. 154(b) by 502 days.

(21) Appl. No.: 13/884,702

(22) PCT Filed: Nov. 11, 2011

(86) PCT No.: PCT/US2011/060453
§ 371 (c)(1),
(2), (4) Date: Jul. 1, 2013

(87) PCT Pub. No.: WO2012/065117
PCT Pub. Date: May 18, 2012

(65) Prior Publication Data
US 2013/0295580 A1    Nov. 7, 2013

Related U.S. Application Data

(60) Provisional application No. 61/413,107, filed on Nov. 12, 2010.

(51) Int. Cl.
*G01N 33/53* (2006.01)
*G01N 33/574* (2006.01)

(52) U.S. Cl.
CPC ..... *G01N 33/57407* (2013.01); *G01N 2333/47* (2013.01); *G01N 2333/4703* (2013.01); *G01N 2333/70596* (2013.01); *G01N 2333/71* (2013.01)

(58) Field of Classification Search
CPC .................. G01N 21/6428; G01N 2021/6421; G01N 21/6486; G01N 2021/6439; G01N 2035/00158; G01N 15/1463; G01N 33/57407; B01L 3/5027; B01L 9/527; G06K 9/00127; G06T 2207/20036; G06T 2207/30024
See application file for complete search history.

(56) References Cited

U.S. PATENT DOCUMENTS

| | | | |
|---|---|---|---|
| 6,297,044 B1 * | 10/2001 | Eisen et al. | ............. 435/287.1 |
| 6,589,779 B1 | 7/2003 | McDevitt | |
| 6,602,702 B1 | 8/2003 | McDevitt | |
| 6,649,403 B1 | 11/2003 | McDevitt | |
| 6,680,206 B1 | 1/2004 | McDevitt | |
| 6,713,298 B2 | 3/2004 | McDevitt | |
| 6,908,770 B1 | 6/2005 | McDevitt | |
| 7,022,517 B1 | 4/2006 | McDevitt | |
| 7,316,899 B2 | 1/2008 | McDevitt | |
| 7,491,552 B2 | 2/2009 | McDevitt | |
| 7,651,868 B2 | 1/2010 | McDevitt | |
| 8,101,431 B2 | 1/2012 | McDevitt | |
| 8,105,849 B2 | 1/2012 | McDevitt | |
| 8,257,967 B2 | 9/2012 | McDevitt | |
| 8,320,996 B2 * | 11/2012 | Panasyuk et al. | ............. 600/473 |
| 8,377,398 B2 | 2/2013 | McDevitt | |
| 2002/0124879 A1 * | 9/2002 | Kaplan | ............... B01L 3/50273 137/13 |
| 2004/0053322 A1 | 3/2004 | McDevitt | |
| 2005/0136548 A1 | 6/2005 | McDevitt | |
| 2006/0073585 A1 | 4/2006 | McDevitt | |
| 2006/0228256 A1 | 10/2006 | McDevitt | |
| 2006/0257854 A1 | 11/2006 | McDevitt | |
| 2006/0257941 A1 | 11/2006 | McDevitt | |
| 2006/0257991 A1 | 11/2006 | Floriano | |
| 2008/0026420 A1 * | 1/2008 | Rimm et al. | ................. 435/40.5 |
| 2008/0038738 A1 | 2/2008 | Weigum | |
| 2008/0050830 A1 | 2/2008 | McDevitt | |
| 2008/0219891 A1 | 9/2008 | McDevitt | |
| 2008/0300798 A1 | 12/2008 | McDevitt | |
| 2009/0215072 A1 | 8/2009 | McDevitt | |
| 2009/0258791 A1 | 10/2009 | McDevitt | |
| 2010/0272635 A1 * | 10/2010 | Rodems et al. | ............. 424/1.11 |
| 2010/0291588 A1 | 11/2010 | McDevitt | |
| 2011/0251075 A1 | 10/2011 | McDevitt | |
| 2012/0208715 A1 | 8/2012 | McDevitt | |
| 2013/0130933 A1 | 5/2013 | McDevitt | |

FOREIGN PATENT DOCUMENTS

| | | |
|---|---|---|
| WO | 2004009840 | 1/2004 |
| WO | 2005083423 | 9/2005 |
| WO | 2005085796 | 9/2005 |
| WO | 2007002480 | 1/2007 |

OTHER PUBLICATIONS

Torres-Rendon et al. "Expression of MCM2, geminin and Ki67 in normal oral mucosa, oral epithelial dysplasias and their corresponding squamous-cell carcinomas", British Journal of Cancer, 2009, 100, 1128-1134.*
Weigum, S. E.; Floriano, P. N.; Christodoulides, N.; McDevitt, J. T. ""Cell-based sensor for analysis of EGFR biomarker expression in oral cancer, Lab on a Chip 2007, 7, 995-1003.
Weigum, S.E. et al, "Nano-Bio-Chip Sensor Platform for Examination of Oral Exfoliative Cytology," Cancer Prevention Research 2010, 3, 518-528.

* cited by examiner

*Primary Examiner* — Gary W Counts
(74) *Attorney, Agent, or Firm* — Boulware & Valoir

(57) ABSTRACT

A point of care diagnostic test, device and disposables for determining a patient risk for oral cancer in the same visit that a sample is collected.

3 Claims, 10 Drawing Sheets

ORAL CANCER POINT OF CARE DIAGNOSTICS

PRIOR RELATED APPLICATIONS

This application is a National Phase filing under 35 U.S.C. §371 of International Application PCT/US11/60453, filed on Nov. 11, 2011, which claims priority to U.S. Provisional Application 61/413,107, filed Nov. 12, 2010. Both applications are incorporated herein by reference in their entirety.

FEDERALLY SPONSORED RESEARCH STATEMENT

This invention was made with government support under Grant No: RC2-DE20785, awarded by the NIH. The government has certain rights in the invention.

REFERENCE TO MICROFICHE APPENDIX

Not applicable.

FIELD OF THE INVENTION

This invention generally relates to methods, devices, disposables and systems for point of care diagnosis of oral cancer, and is an improvement on US2008038738, incorporated in its entirety by reference.

BACKGROUND OF THE INVENTION

All squamous cell carcinoma lesions are thought to begin via the repeated, uncontrolled division of cancer stem cells of epithelial lineage or characteristics. Accumulation of these cancer cells cause a microscopic focus of abnormal cells that are, at least initially, locally confined within the specific tissue in which the progenitor cell resided. This condition is called squamous cell carcinoma in situ, and it is diagnosed when the tumor has not yet penetrated the basement membrane or other delimiting structure to invade adjacent tissues. Once the lesion has grown and progressed to the point where it has breached, penetrated, and infiltrated adjacent structures, it is referred to as "invasive" squamous cell carcinoma. Once a carcinoma becomes invasive, it is able to spread to other organs and cause a metastasis or secondary tumor to form.

Oral cancer is a subtype of head and neck cancer and is any cancerous tissue growth located in the oral cavity. It may arise as a primary lesion originating in any of the oral tissues, by metastasis from a distant site of origin, or by extension from a neighboring anatomic structure, such as the nasal cavity. Oral cancers may originate in any of the tissues of the mouth, and may be of varied histologic types: teratoma, adenocarcinoma derived from a major or minor salivary gland, lymphoma from tonsillar or other lymphoid tissue, or melanoma from the pigment-producing cells of the oral mucosa. There are several types of oral cancers, but around 90% are squamous cell carcinomas, originating in the tissues that line the mouth and lips.

Oral squamous cell carcinoma (OSCC) is a global health problem afflicting close to 300,000 people each year. Despite significant advances in surgical procedures and treatment, the long-term prognosis for patients with OSCC remains poor, with a 5-year survival rate at approximately 50%, which is among the lowest for all major cancers. High mortality associated with OSCC is often attributed to advanced disease stage at diagnosis, underscoring the need for new diagnostic methods targeting early tumor progression and malignant transformations.

SUMMARY OF THE INVENTION

Our initial proof of concept work was described in Weigum, S. E. et al., Nano-Bio-Chip Sensor Platform for Examination of Oral Exfoliative Cytology, Cancer Prevention Research 2010, 3, 518-528, expressly incorporated by reference. However, these initial experiments were primitive, in that they did not employ a standard disposable card, used bench top fluidics and examined only a single biomarker. This invention has now been improved to use a disposable card containing reagents, a commercially available analyser, and a panel of biomarkers are analyzed, as described below.

We have developed a programmable bio-nano-chip that allows for the analysis of cellular samples obtained from a minimally invasive brush biopsy sample. This invention describes an improved panel of biomarkers to cover early oral cancer detection and progression, and the technology also has applications into potential rare cell detection. The cell suspensions allow for the simultaneous quantification of cell morphometric data and expression of molecular biomarkers of malignant potential in an automated manner using refined image analysis algorithms based on pattern recognition techniques and advanced statistical methods. The device has at least 90% specificity and 90% sensitivity, preferably at least 92, 93, 94, 95, 96, or 97%.

The chip-based platform is adapted to include a panel of biomarkers indicative of dysplasia as derived from cytomorphometric and molecular data. As such the programmable bio-nano-chip will be augmented with customized panels of the tumor markers alphaV beta6, Epidermal Growth Factor Receptor (EGFR), Ki67, Geminin, Mini Chromosome Maintenance protein (MCM2), Beta Catenin, and EMMPRIN (CD147). Expression of those markers has already been shown to correlate with increasing dysplasia and malignant change (conversion to cancer).

To summarize the invention, the diagnostic is performed on a portable device together with disposable biochips, that contains various liquid and/or dried reagents. The analyzer device contains microfluidics for sample and reagent flow, means for detecting signals, usually light based signals, computing means for analyzing collected data and usually means for inputting patient information and displaying final results.

Generally speaking, the disposable lab cards contain a detection window which has a membrane therein sized to capture cells. In preferred embodiments, this membrane is exchangeable, e.g., with membranes of differening size, or with arrays of antibodies, and thus is contained inside a hinged door or lid or similar components that serves to lock the exchangeable component into the card.

An inlet port is fluidly connected to the detection window, and sample is applied and travels to the window where cells are trapped by the membrane. The card preferably also contains regent chambers, although simple cards have been tested without same, and the analyser activates the reagent chamber, pushing wash fluid to the detection window to wash away cell debris as needed. Next, a second reagent chamber is activated, and travels past a dry pad or chamber containing dry antibodies and stains, reconstitutes same and carries these to the detection window, where the cells are stained with nuclear, cytoplasmic and antibody stains. Optionally, these reagents can be premixed with the second chamber fluid, but stability of antibody components is improved in the dry form. Preferably these dry pads are also exchangeable, e.g. via a hinged lid. The excess reagents can then be washed away, using wash from the first chamber, and the remaining signals detected and analyzed. Additional detection windows can be provided, depending on the number of analytes to be analyzed and the spectral range of the signals (and device capacity to distinguish same). Alternatively, the cells can be serially stained, and then washed clean and restrained.

These disposable lab cards are not detailed beyond this basic description, but are described more fully in U.S. Ser. Nos. 61/484,492, filed May 10, 2011, and 61/558,165, filed Nov. 10, 2011, and each expressly incorporated by reference in its entirety for all purposes.

The card shape, size and fluidics and placement of chambers or blisters will of course vary according to the analyzer selected. The analyzer can be any desk top analyzer, or a commercially available brand, such as that by LABNOW™ (Austin Tex.) or Force Diagnostics™ (Chicago, Ill. and Houston, Tex.). Other devices and systems can be used and are e.g., described in WO2007002480, WO2005083423, WO2004009840, WO2005085796 and US2009215072.

In preferred embodiments a suspension of cells is collected with a rotating brush. Our research has indicated that collecting cells in the way is sufficient to permeabilize the cells for our purposes, but it is also possible to fix and permeabilize the whole cells in the usual way. The cells can be collected on a membrane that allows debris to pass through, but not whole cells. Alternatively, it is also possible to enrich for a particular population of cells with e.g., magnetic beads coupled, e.g., to a receptor or cell surface proteins, such as an antibody for EGFR. This can be done in a pre-chamber before reaching the detection window. Then when the magnet is turned off, the enriched cancer cells can pass to the image cytometer. Using this technique we have already been able to detect a single cell in 10,000 and we expect that we can easily get to $10^6$ and $10^9$ sensitivity when fully optimized.

The system then detects a variety of morphological and biological markers, including for example, DAPI for DNA, and phalloidin for F-actin. These two stains provide a great deal of information about cell morphology, and for example, nuclear to cytoplasm size or diameter ratios (important indicators that a cell is transforming) and cell shape (cancer cells are rounder). Other parameters that can be measured and used in the model include but are not limited to:

Area (WCArea[red])—Area of Whole cell selection in square pixels determined in red from Phalloidin stain.

Mean Intensity Value (WCMean[red], [green])—Average value within the WC selection. This is the sum of the intensity values of all the pixels in the selection divided by the number of pixels. [red] has QA/QC value and [blue] has limited descriptive value, whereas [green] is the most important for surface markers. For intracellular markers, the NuMean[green] is most descriptive.

Standard Deviation (WCStdDev[red], [green])—Standard deviation of the intensity values used to generate the mean intensity value. [red] useful for Phalloidin, QA/QC and descriptive, [green] for surface markers.

Modal Value (WCMode[red], [green])—Most frequently occurring value within the selection. Corresponds to the highest peak in the histogram. Similar to Mean in terms of value.

Min & Max Level (WCMin and WCMax[red], [green], [blue]—Minimum and maximum intensity values within the selection. This parameter has limited descriptive value, but may be used for quality assurance (QA), quality control (QC).

Integrated Density (WCIntDen[red], [green], [blue])—Calculates and displays "IntDen" (the product of Area and Mean Gray Value)—Dependent values.

Median (WCMedian[red], [green])—The median value of the pixels in the image or selection. This again is similar to Mean and Mode in terms of utility.

Circ. (circularity): $4\pi^*area/perimeter^2$. A value of 1.0 indicates a perfect circle. As the value approaches 0.0, it indicates an increasingly elongated shape. Values may not be valid for very small particles.

AR (aspect ratio): diameters of major_axis/minor_axis.

Round (roundness): $4^*area/(\pi^*major\_axis^2)$, or the inverse of the aspect ratio.

Other parameters may include percentages of cells with one or more parameters meeting certain criteria, or above a certain cut-off.

Cells can also be stained with labeled antibodies for the various cancer markers discussed herein. Generally, different biomarkers should be labeled with different labels, so that they can be distinguished. However, some overlap is allowable where the markers are spatially distinguished in the cell, e.g., EGFR on the cell surface and Ki67 in the nucleus. Alternatively, the chip can be divided into two or three portions (or two chips used) and separate groups of labels employed, or the chip can have multiple detection windows or portions thereof having separate fluidics.

The following abbreviations are used herein:

| Abbreviations | |
|---|---|
| Ab | Antibody |
| ABS | Acrylonitrile butadiene styrene |
| AUC | Area under the curve |
| AVB6 or αVβ6 | Alpha V beta 6, an integrin |
| BM | Biomarker |
| DNA | Deoxyribonucleic acid |
| EGFR | Epidermal Growth Factor Receptor |
| EMMPRIN | Extracellular Matrix Metalloproteinase Inducer, aka CD147 |
| FITC | Fluorescein isothiocyanate |
| HNSCC | Head and neck squamous cell carcinomas |
| IVD | in vitro diagnostic device |
| Ki67 | Antigen KI-67 also known as Ki-67 or MKI67 is a protein that in humans is encoded by the MKI67 gene |
| LOD | Limits of detection |
| MAB | Monoclonal Ab |
| MCM2 | Mini Chromosome Maintenance protein 2 |
| N/C ratio | nuclear/cytoplasmic ratio |
| NBC | Nano-bio-chip |
| NPV or PV⁻ | Negative predictive value |
| NSE | Neuron-specific enolase |
| OSCC | oral squamous cell carcinoma |
| PBSA | Phosphate buffered saline with bovine serum albumin |
| PML | potentially malignant lesions |
| PNBC | Programmable BNC |
| PPV or PV⁺ | positive predictive value |
| PV | Predictive value |
| RNA | Ribonucleic acid |
| ROC | Receiver operating characteristic. A graphical plot of the sensitivity, or true positive rate, vs. false positive rate (1 - specificity or 1 - true negative rate), for a binary classifier system as its discrimination threshold is varied. The ROC can also be represented equivalently by plotting the fraction of true positives out of the positives (TPR = true positive rate) vs. the fraction of false positives out of the negatives (FPR = false positive rate). Also known as a Relative Operating Characteristic curve, because it is a comparison of two operating characteristics (TPR & FPR) as the criterion changes. |
| ROI | Region of interest |
| Wnt | Proto-oncogene protein Wnt |

-continued

| Abbreviations | |
|---|---|
| β-catenin | Beta Catenin is a protein that in humans is encoded by the CTNNB1 gene |

The word "morphometric" as used herein means the measurement of such cellular shape or morphological characteristics as cell shape, size, nuclear to cytoplasm ratio, membrane to volume ratio, and the like.

The word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

Z merging of p focal planes for each location

QA/QC on Z merging (replaces Z-merged if faulty with appropriate single Z image) or discards if no appropriate image found.

Cell recognition through contouring, dynamic thresholding, masks, intensity and size filters, segmentation algorithms for the resulting images. Removal of debris, background subtraction, identification of cells with no cytoplasm stain, i.e. "lone nuclei" to be tagged for later possible discrimination. The process concludes with collection of X parameters in each of the 3 color channels for each pair of cell cytoplasm and corresponding nucleus defined from analysis as area of interest for cytoplasm (AOI cyto), and area of interest for nucleus (AOI nucleus)

Figure 8:
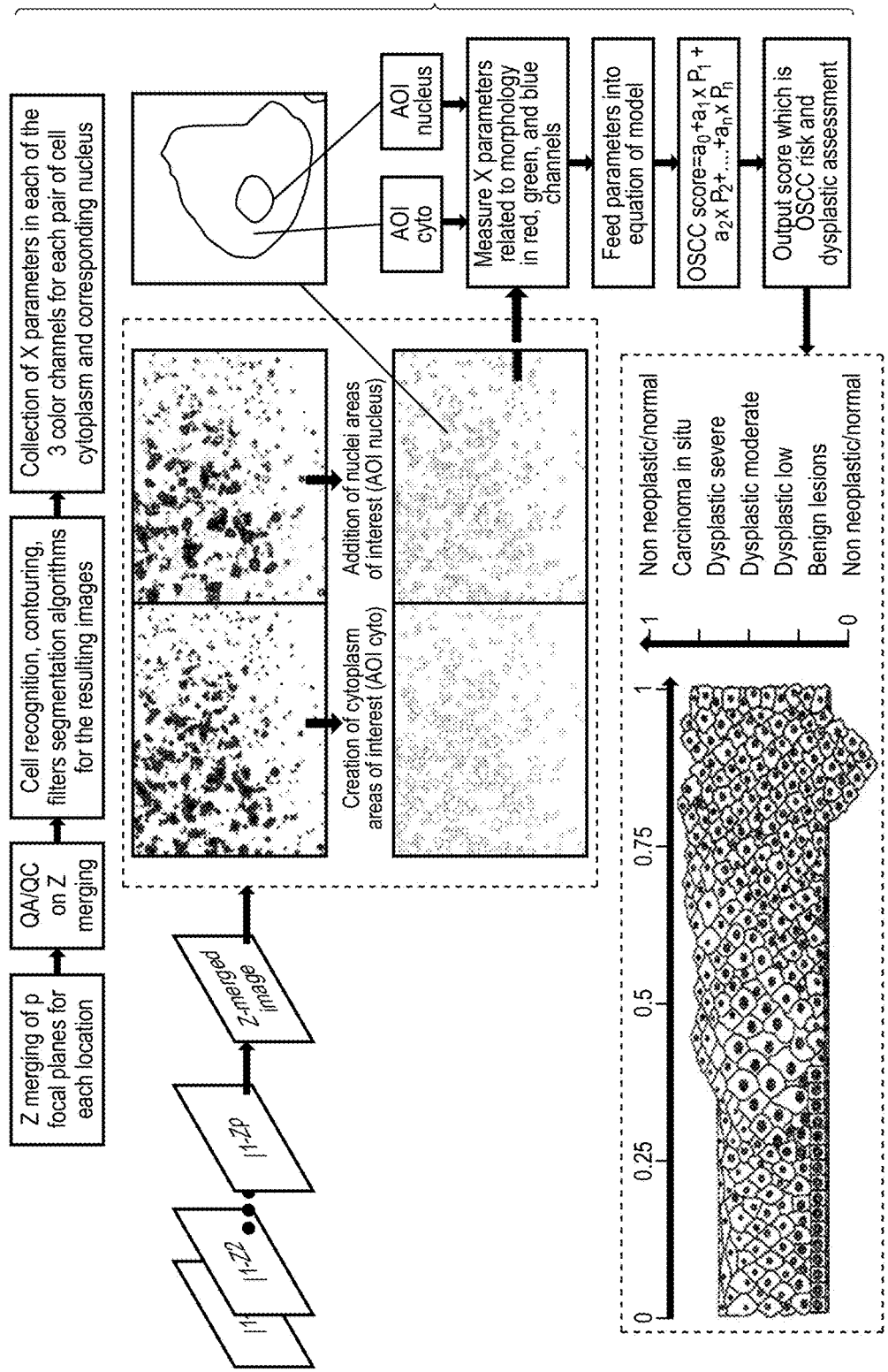

FIG. 8. Schematic showing detailed image processing. The process is detailed here with the first step of Z-merging, followed by QA/QC on the merged images. Cell recognition is achieved through a series of image treatments and algorithms that first identify the cells cytoplasm boundaries, and resolve the potential overlap between the cells. When too many cells are present, overlapped cells that cannot be resolved are discarded. Legitimate cells will be cells of a given size range, and which have only one nucleus. From these images, areas of interest (AOI) for both the nucleus and the cell cytoplasm are recorded. Each of these AOIs is then interrogated for the list of parameters listed above in each of the three colors. Additional parameters can consist of status (1 or 0) or certain cells based on parameters cut-off values. This allows for after the fact filtering of the data according to certain criteria. Final values for all parameters are then fit into a logistic regression type equation that weighs each factor in order to produce a score corresponding to oral cancer risk:

$$\text{OSCC score} = a_0 + a_1 \times P_1 + a_2 \times P_2 + \ldots + a_n \times P_n$$

where $a_{1 \to n}$ are weighing coefficients, and $P_{1 \to n}$ are parameters (logged or not) related to morphology or molecular expression. This score can be normalized to a value between 0 and 1 corresponding to the malignant progression between normal (0) and oral cancer (1) through the dysplastic changes according to the scale shown.

Figure 9:
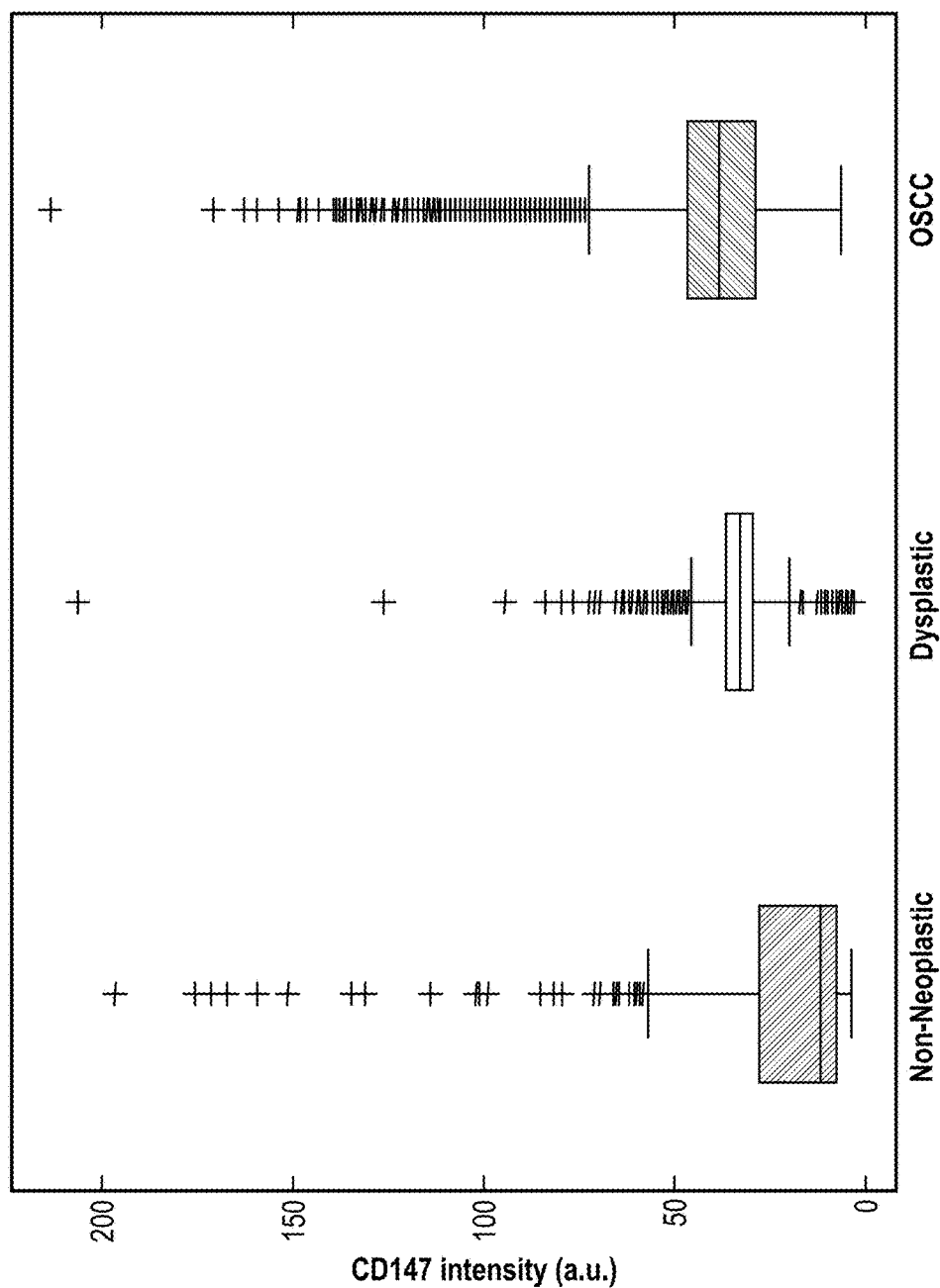

FIG. 9. Preliminary data is shown with the intensity of the surface biomarker EMMPRIN (CD147) exhibiting the ability to distinguish between non-neoplastic categories (normal and benign), dysplastic, and oral cancer.

DETAILED DESCRIPTION OF THE INVENTION

This invention describes an expanded panel of biomarkers to cover early detection and progression of oral cancer. We analyze cellular samples obtained from a minimally invasive brush biopsy sample, simultaneously quantifying cell morphometric data and expression of molecular biomarkers including at least 2, 3 4, 5, 6 or all of AVB6, EGFR, Ki67, Geminin, MCM2, Beta Catenin, and EMPPRIN. The programmable bio-nano-chip approach will be compared to the current standard of care based on biopsy and histopathological assessment of the lesions to validate the new method.

The analysis will be performed using a hand held device with disposable chip that provides a rapid, cost effective, yet sensitive method of detecting these tumor markers. Additionally, because of its portability, low cost, and speed, this approach can function in point of care settings using non-invasive brush biopsy samples. The invention therefore also includes the disposable chip with reagents placed thereon that are specific for measuring the above markers. The device contains power, detection of signal, programming, and capacity to display the final results.

Brush biopsies from two-thirds of the subjects are being used in the development of the programmable bio-nano-chip system and samples from the remaining one-third of subjects will be used in clinical validation of the PNBC system. The primary outcome for the study is to confirm the diagnostic sensitivity and specificity of the PNBC system in distinguishing between non-neoplastic, dysplastic, and malignant lesions when compared against the gold standard results provided by scalpel biopsies and histopathological assessments.

This novel programmable bio-nano-chip approach has the potential to turn around biopsy results in a matter of minutes as compared to days for traditional pathology methods. To finalize this model, a total of 950 patients who present for the scalpel biopsy of a suspicious oral lesion are being recruited at three clinical sites. A second clinical trial is also underway to test this model in a population recruited at primary care settings, which better represents the prevalence of the disease in the general population. For these trials, two brush biopsies will be performed—one on the oral lesion and another on normal appearing mucosa.

Example 1

Proof of Principle

Using some of the same concepts borrowed from our HIV immune function test, we adapted the flow cell for use with brush biopsy samples to explore the cytomorphometric features and biomarker signatures for their capacity to distinguish between oral cancer and benign lesions. The PNBC sensor system for assessing OSCC integrates multiple laboratory processes onto a microfluidic platform in three primary steps: 1) cell separation/capture on the membrane filter, 2) biomarker immunolabeling and cytochemical staining, and 3) fluorescent imaging and analysis. No human intervention is needed once the sample is applied to the device, until the results are obtained, and the method is fully automated.

During cell capture, an oral cytology suspension is delivered to the PNBC sensor, using pressure-driven flow, whereupon any particles or cells larger than the membrane pore size are retained on the micro-membrane surface. Once captured, the cells are serially fluorescently stained in a very rapid process.

The cells are then detected using fluorescence microscopy in an X, Y, Z scan of the membrane surface. Monochrome images of Phalloidin, epidermal growth factor receptor (EGFR), and DAPI fluorescent labels are collected sequentially using appropriate filter cubes, then merged into red, green, and blue spectral channels, respectively. Multiple Z-focal planes are collected at +5 μm intervals and recombined using an automated z-stack focusing algorithm in ImageJ in order to accommodate adherent epithelial cell populations with both individual and aggregated cell clusters.

Automated image analysis routines utilize ImageJ and/or Cell Profiler open-source software with custom written macros for quantitative intensity standardization and cell/nuclear contouring to define the region-of-interest (ROI) for each object/cell. The cytoplasm is stained fluorescent red with phalloidin (red), the nucleus blue with DAPI, and any cancer biomarker (e.g. EGFR) immunofluorescently stained green with FITC labeled monoclonal antibody.

TABLE 1

Assay reagents applied in the BNC assays for oral cancer.

| BIOMARKERS | SUPPLIER AND PRODUCT # | STOCK CONCENTRATION | WORKING CONCENTRATION (IN PBSAT) |
|---|---|---|---|
| EGFR AB-10 (MOUSE MAB - CLONE 111.6) | THERMO SCIENTIFIC - LABVISION #MS-378-P CLONE: 111.6 | 200 µG/ML IN PBS | 10 µG/ML |
| ANTI-HUMAN EMMPRIN | R AND D SYSTEMS CATALOG# AF972 | 100 µG (DILUTED IN 0.5 ML PBS FOR 200 µG/ML CONCENTRATION) | 10 µG/ML |
| AVB6 | MILLIPORE CATALOG# MAB2074Z CLONE: E7P6 | SIZE: 100 µG CONCENTRATION: 1 µG/ML | 50 µG/ML |
| KI67 | DAKO CATALOG# M7240 CLONE: MIB-1 | SIZE: 200 µL | 1:25 |
| GEMININ | ABCAM CATALOG# AB12147 | SIZE: 100 µl CONCENTRATION: 0.5 MG/ML | 10 µG/ML |
| MCM2/BM28 | BD TRANSDUCTION LABS CATALOG# 610701 CLONE: 46/BM28 | SIZE: 150 µG CONCENTRATION: 250 µG/ML | 10 µG/ML |
| B-CATENIN | BD TRANSDUCTION LABS CATALOG# 610154 CLONE: 14 | SIZE: 150 µG CONCENTRATION: 250 µG/ML | 10 µG/ML |

Subsequent automated image analysis routines (see FIGS. 7 and 8) employ digital filtering and image segmentation of the DAPI and Phalloidin signals, blue and red spectral channels, respectively, to generate binary masks and contours of the nuclear and cytoplasmic ROIs for measurement in all fluorescent channels. This fully automated programmable bio-nano-chip methodology permits concurrent analysis of EGFR surface biomarker expression and cellular/nuclear morphology using over 50 ROI intensity and shape parameters with particular attention focused on the cellular and nuclear area, the nuclear/cytoplasmic (N/C) ratio, and mean cellular EGFR intensity as early indicators of malignancy.

A total of 52 oral brush cytology specimens from healthy and disease participants were collected from the University of Texas (UT) Health Science Center at San Antonio, Utah Dental Branch at Houston, and UT at Austin. Each individual parameter was evaluated by a receiver operating characteristics (ROC) curve. Reagents were as in Table 1.

All parameters tested exhibit significant capacity for disease classification and discrimination between patients with OSCC or dysplasia versus healthy controls or benign conditions, as demonstrated by the area under the curve (AUC) values greater than 0.5. The ROC curve generated from the predicted values obtained from logistic regression models in the combined biomarker panel exhibited an AUC value of 0.94 with a projected 97% sensitivity and 93% specificity for detection and classification of malignant and pre-malignant oral lesions.

These promising proof of principle data demonstrate the efficacy of brush biopsy and programmable bio-nano-chip analysis to distinguish oral cancer from normal oral mucosa. This expansion addresses the more significant clinical problem of distinguishing between normal oral mucosa, dysplastic lesions, non-dysplastic lesions, and malignant lesions. To maximize the sensitivity and specificity of PROGRAMMABLE BIO-NANO-CHIP, particularly for pre-malignant lesions, a broader panel of tumor and dysplasia markers alongside cell morphometric analysis is implemented.

Example 2

Additional Markers

According to the Oral Cancer Foundation, HPV is now the leading cause of oral cancers in the US. Indeed, while tobacco continues to be an important risk factor, an increasing number of never-smoker patients have been diagnosed with oral cancer, developed by HPV16 infection. The system demonstrated here allows for future implementation of additional markers already discovered, emerging, or that will be discovered, that could specify HPV-related oral cancers.

The Speight and Thornhill team's long track record of research into the mechanisms associated with the malignant conversion of oral keratinocytes has enabled identification of specific markers of malignant conversion. Integrins are a family of molecules that are important in cell-cell and cell-matrix interactions for which the importance of cell surface integrin expression, particularly the expression of $\alpha_v\beta_6$ by oral keratinocytes, in the development of a malignant phenotype and invasion of the connective tissue has been demonstrated. Indeed, it has been shown that $\alpha_v\beta_6$ expression correlates with the degree of dysplasia in lesions and is greatest in those lesions that progress and in invasive oral cancers.

In normal eukaryotic cells, chromosomal replication is tightly regulated and coupled to progression through cell cycle. Minichromosome maintenance (MCM) proteins are present in all phases of cell cycle, but are absent in quiescent, terminally differentiated, and senescent "out-of-cycle" states. The MCM proteins, therefore, represent a new class of proliferation marker. It has been shown recently that MCM proteins are dysregulated in a wide range of pre-neoplastic and neoplastic states, representing powerful tumor markers in a range of organ systems including cervix, esophagus, bladder, prostate, and brain. The Sheffield team has shown that MCM proteins MCM2 and geminin, and more traditional cell proliferation marker Ki67, are over expressed in salivary tumors and oral cancers, and perhaps more importantly that levels of these markers were elevated in dysplastic lesions with values that distinguished them from both NOM and OSCC. A similar situation has been noted for pre-malignant genito-urinary lesions with elevated levels of Mcm5 being highly predictive for development of genito-urinary tract cancer. Preliminary data shows MCM5 may play a similar role in oral lesions.

Further, animal models developed by Vigneswaran showed that expression of biomarker EMMPRIN gradually increases during tumorigenesis, closely simulating its expression pattern in human HNSCC tumorigenesis. The Wnt-β-catenin pathway is frequently deregulated in oral cancer, which is identified by nuclear localization of β-catenin. Importantly, addition of integrins and MCM proteins along with other tumor markers, such as EGFR, CD147, β-catenin, and cell proliferation marker Ki67, could significantly enhance sensitivity and specificity of brush biopsy analysis for both oral cancer and pre-cancer.

Example 3

Applications

The innovative aspect to the validation of multiple biomarkers (separately or in a multiplex manner) for differentiating potentially malignant lesions is the application of a minimally-invasive brush biopsy test that can be performed in clinics or dentist's offices. Results will be available in a matter of minutes, versus hours to days for scalpel biopsies or OraScan analyses of brush biopsy samples.

The new device is intended to serve as a diagnostic device and not simply a screening aid for patients that have potentially malignant lesions (PMLs). In this context the new device is meant to replace (or augment) the current scalpel biopsy and pathology exam that now takes more than three days to complete.

Unlike the highly invasive scalpel biopsy, the new bio-nano-chip device will collect samples with a noninvasive, soft cytology brush and in doing so will be compatible with sampling of multiple areas.

These new devices have potential for broad usage in a number of settings where the diagnosis of intra oral soft tissue is necessary with particular emphasis on PMLs. Three settings are identified for the new device as follows:

The primary care setting would involve general dental practices or primary care medical practices. Most patients with suspicious lesions causing symptoms will first present to a primary care clinician or a symptomless lesion may be fortuitously identified in primary care as a result of a routine dental or medical examination. These lesions currently pose a diagnostic dilemma for the primary care clinician i.e. should the lesion be managed in primary care, observed, referred to a specialist as a routine referral or referred as an urgent priority?

Since an incisional biopsy is currently the only test with sufficient diagnostic sensitivity and specificity to distinguish between these categories, many more patients are referred for urgent specialist attention than is necessary. This is because i) most primary care clinicians do not have the expertise to perform the biopsy, ii) the time it would take, and iii) the biopsy is better performed by the specialist if they are to be involved in the further treatment of the patient.

The new technology will enable the primary care clinician to obtain quantitative diagnostic information about the lesion, whilst the patient is still in their office, and help direct their decision about how to manage the patient. It will ensure far fewer unnecessary specialist referrals and for those patients that do require specialist referral it will be possible to decide the degree of urgency of referral and to provide the specialist with quantitative data to support this decision. For patients that the primary care clinician elects to manage or observe themselves, they will be able to make this decision with a far higher degree of certainty and the option to re-test using the technology at any time.

Most specialists in secondary care would perform a biopsy on a suspicious lesion for definitive diagnostic purposes. However, suspicious lesions are often large or multiple and identifying the 'best' site to biopsy can be challenging. There is always the concern that a malignancy has been missed because the area biopsied was not the 'right' site. Thus, it is likely that the technology would be used slightly differently in secondary care than in primary care. Here it is probably that large or multiple lesions regarded as highly suspicious would be subjected to brush biopsy and point of care lab-on-a-chip diagnosis in order to identify the best site to subject to an incisional biopsy. It is also likely that many lesions that clinically appear benign would be subjected to the new technology to provide some quantitative confirmation of the subjective clinical appearance. Many lesions that are not malignant, but following an incisional biopsy are found to be dysplastic, and have the potential to progress to malignancy, are carefully monitored in secondary care. Regular repeat incisional biopsy of such lesions to monitor if the lesion is getting better or worse or to see if it is responding to treatment is difficult, costly and very unpleasant for the patient. The new technology, however, would make it far more practical to monitor such lesions on a regular basis.

Patients diagnosed with oral cancer would normally be referred to tertiary care surgeon or multidisciplinary team including oncologists, surgeons etc. for definitive treatment of their cancer and monitoring for recurrence. In this setting the technology may be used to multiply sample lesions prior to surgery in order to map out surgical margins and post surgery to monitor patients for any recurrence.

Resource poor settings often lack the more advanced secondary and tertiary referral centers, pathology services etc. that would complete the full diagnosis of suspicious oral lesions in developed countries like the US. The new technology is robust and portable making it ideal for use in the field and other resource poor settings. In such settings, the ability to diagnose lesions with a high degree of certainty, within a few minutes and at the point of contact with the patient, would enable healthcare to quickly identify patients on whom scarce healthcare resources should be focused.

Figures 1A, 1B:
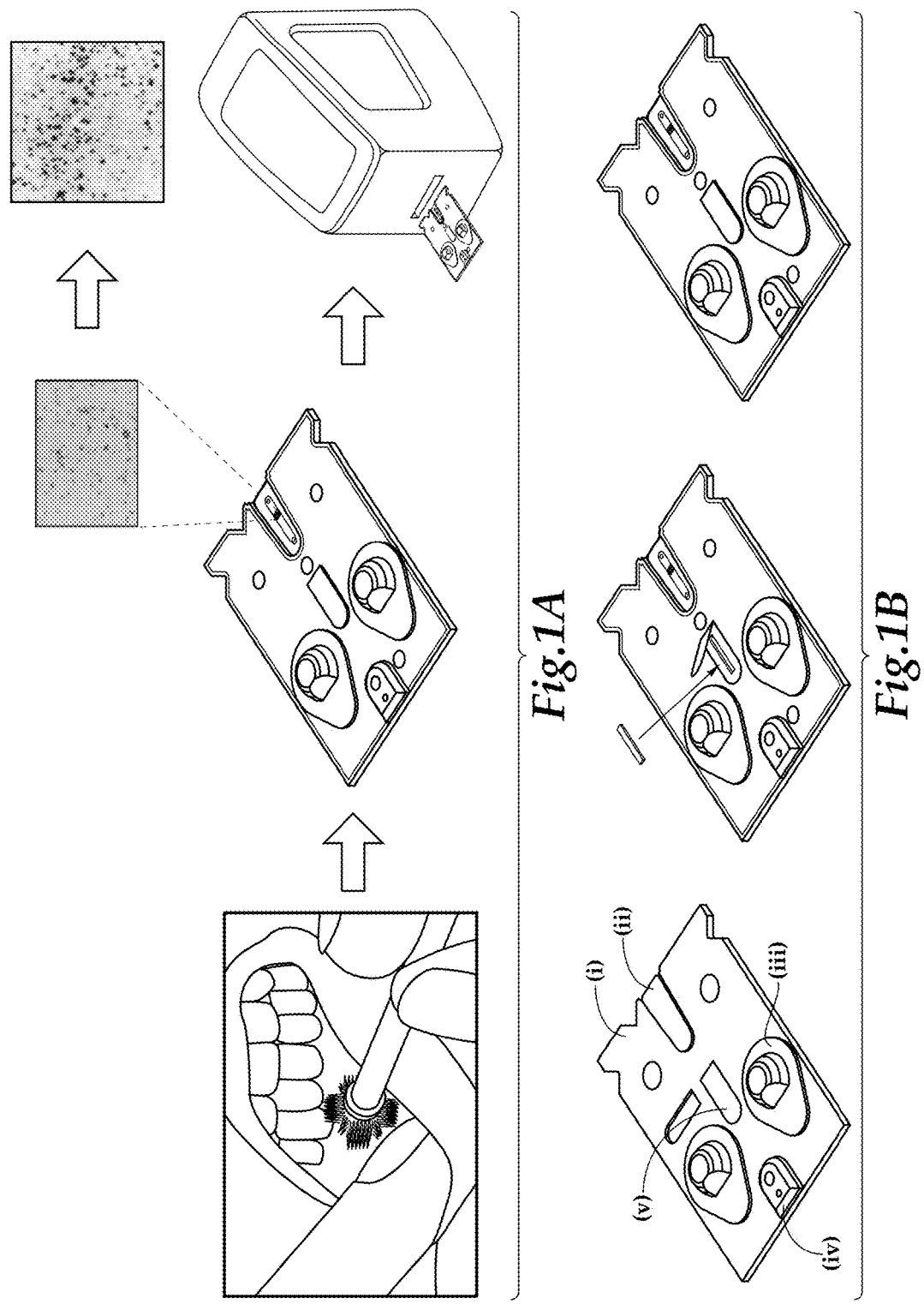
FIG. 1A is a bio-nano-chip system that includes lab card, and analyzer. The single marker or multi-marker oral cancer bio-nano-chip is an in vitro diagnostic device (IVD) that includes lab card, assay and analyzer, intended to simultaneously identify and quantitate the level of expression of a panel of biomarkers for dysplasia and cancer including alphaV beta6, Epidermal Growth Factor Receptor (EGFR), Ki67, Geminin, Mini Chromosome Maintenance protein (MCM2), Beta Catenin, and EMPPRIN (CD147), as well as cytomorphometric parameters such as nuclear area, nuclear to cytoplasm ratio, and other cell-based morphological characteristics to yield a multi-marker signature using cells collected with a minimally invasive brush biopsy approach. The small insets show cells capture by the membrane, and cells with fluorescent stain.
FIG. 1B shows an exemplary card in additional detail. The BNC assay card is composed of a number of modular subassemblies, including (1) multilayered microfluidics card, (if) bead support chip, (iii) two fluid filled blister packs, and (iv) a sample input port. Solid state pad-based reagents are added to the card after fabrication via an access ports on the card's surface (v). Here, the modular and programmable nature of the design allows the PBNC to be reconfigured to accommodate new detection modalities without changing the underlying microfluidic architecture of the LOC. The card is designed to interface with a compact and portable analyzer that integrates the mechanical, electrical, and optical components necessary for analysis. Together the three components constitute a compact field-deployable bead-based assay system capable of highly multiplexed quantitative analysis of complex fluids such as serum and saliva.
Figure 1C:
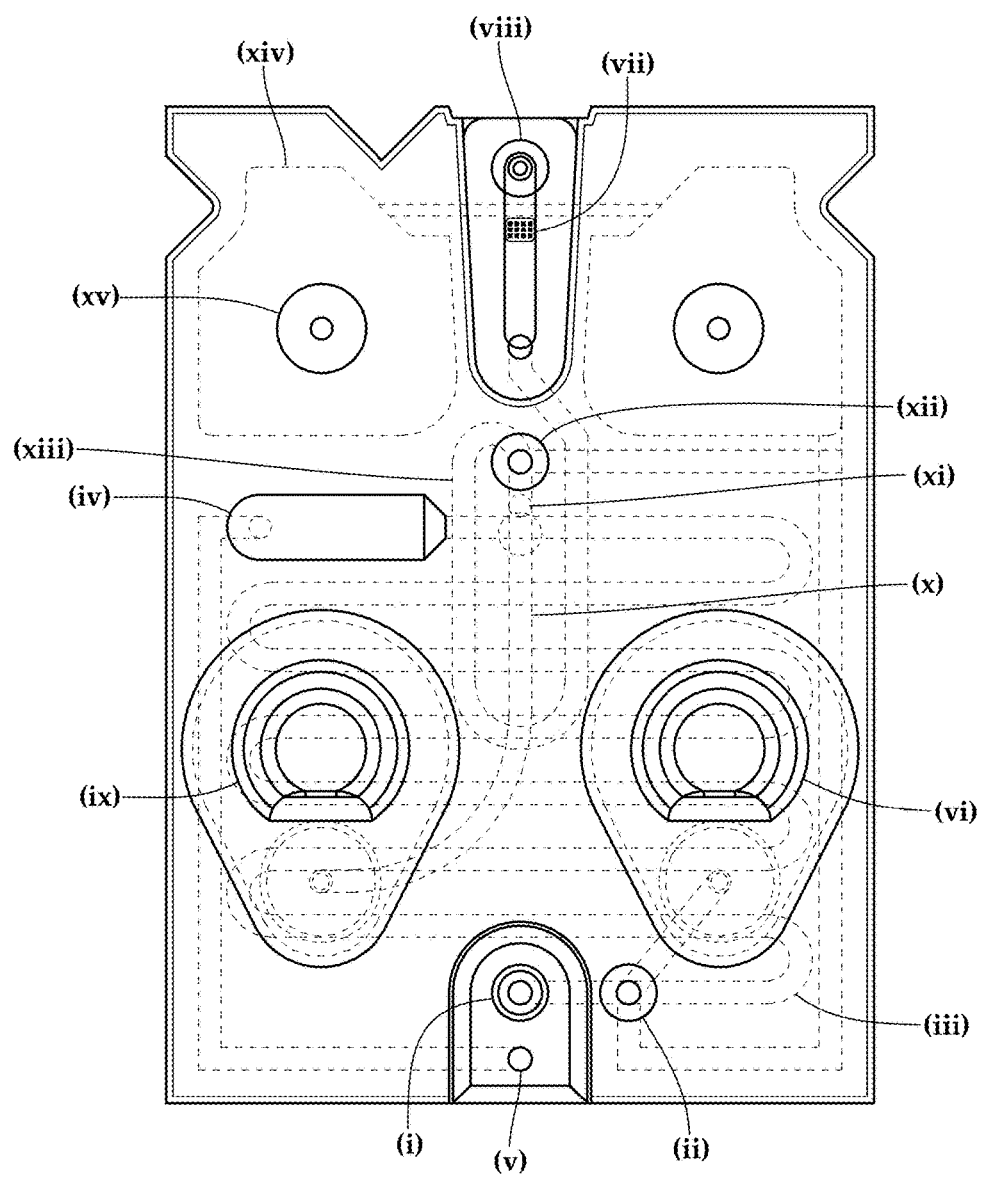
FIG. 1C shows a second generation card with improved microfluidics, bubble traps, herringbone mixers, vents, and the like. A piping diagram of the PBNC's microfluidic network shows the principle microfluidic channels and features. The sample metering channel features a port for sample input (1) configured with an inline membrane filter, a bubble trap (ii), a metered sample loop (ii1), and a sample overflow chamber (iv) leading to an external vent (v). The right-hand fluid containing blister pack (vi) intersects the sample loop to evacuate the metered portion of sample toward the membrane housed in the detection window (vii). Air behind the array is purged through a wetting vent (viii). The reagent preparation channel links the left-hand containing blister (ix) to a solid-state reagent storage chamber (x) followed by an inline track-etch membrane filter (xi) and bubble trap (xii). Both the sample metering channel and reagent preparation channel confluence at the distal bubble trap, which forms a junction column with a single output. The common channel features six staggered herringbone mixer sets (xiil) configured asymmetrically on the top and bottom channel substrate leading to the bead sensors. The drain to the analysis chamber directs all flow to a large capacity bilateral waste reservoir (xiv). The waste reservoir vents (xv) are covered with selectively permeable vent membranes for secure waste containment.
Figure 2:
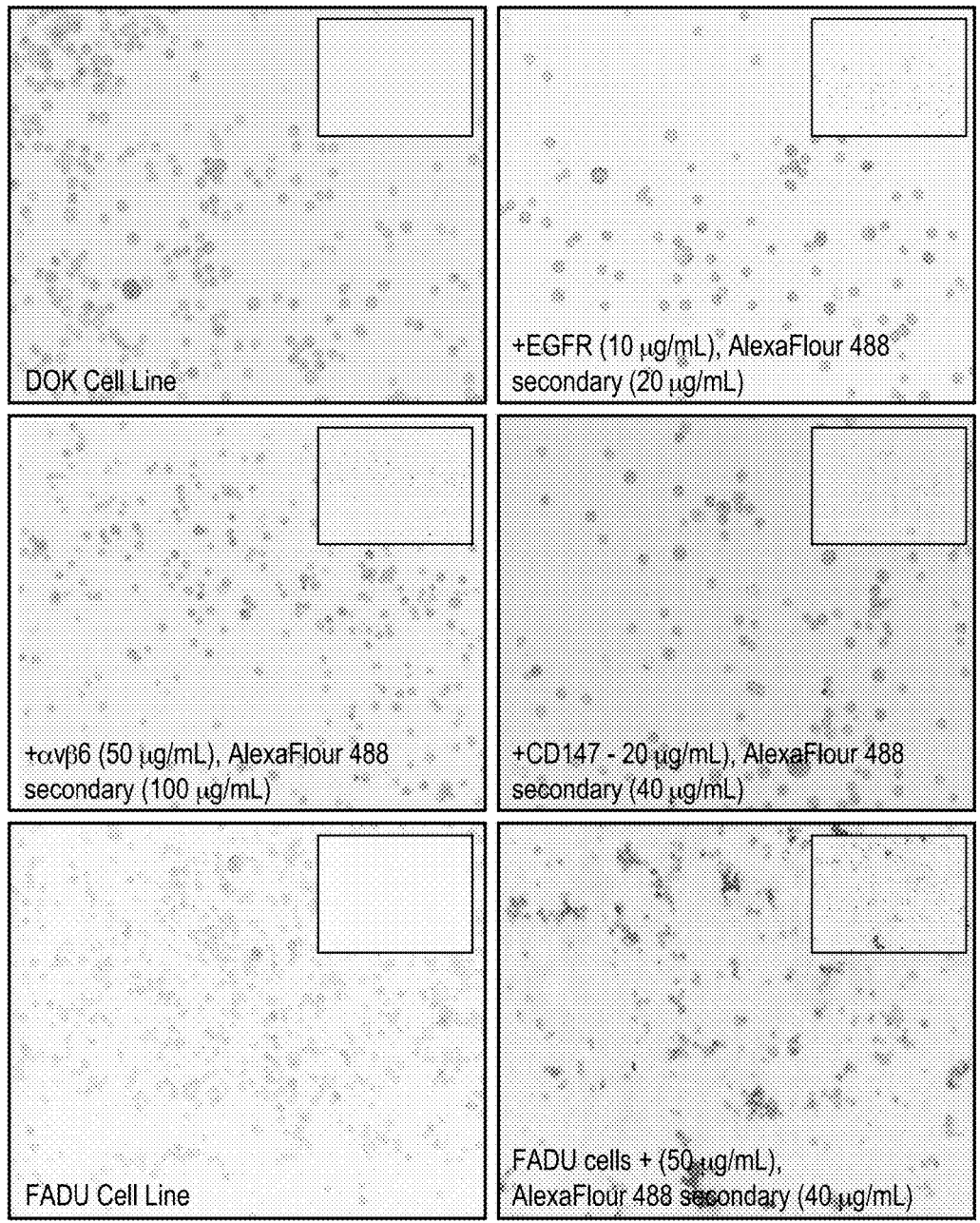
FIG. 2 Microphotographs obtained for various biomarker assays on the programmable bio-nano-chip platform.

Assays for EGFR, as well as proof of concept for new biomarkers αvβ6, CD147 and Ki67 are shown below in FIG. 2, as imaged on the programmable bio-nano-chip. For each of these assays, cells were captured on the surface of the membrane, subjected to a cocktail of a primary antibody to the biomarker in PBSA and Tween 20, and then to a secondary antibody cocktail consisting of an AlexaFluor-488 (green) conjugated antibody, as well as DAPI and Phalloidin for morphometry. The green spectral channel is shown in the inset for the DOK cell line in the presence of irrelevant antibody, EGFR, αvβ6, and CD147, showing adequate staining of the cells in this system. The Ki67 biomarker assay was developed with the FADU cell line (bottom row), which shows great nuclear staining in the green channel (bottom right).

Additional features of this approach enable detection of rarer cell events. We have mixed different ratios of two cancer cell lines, MDACC 435, expressing with very low (5%) expression of EGFR and MDACC 468 cells with very high expression of EGFR.

Figure 3A:
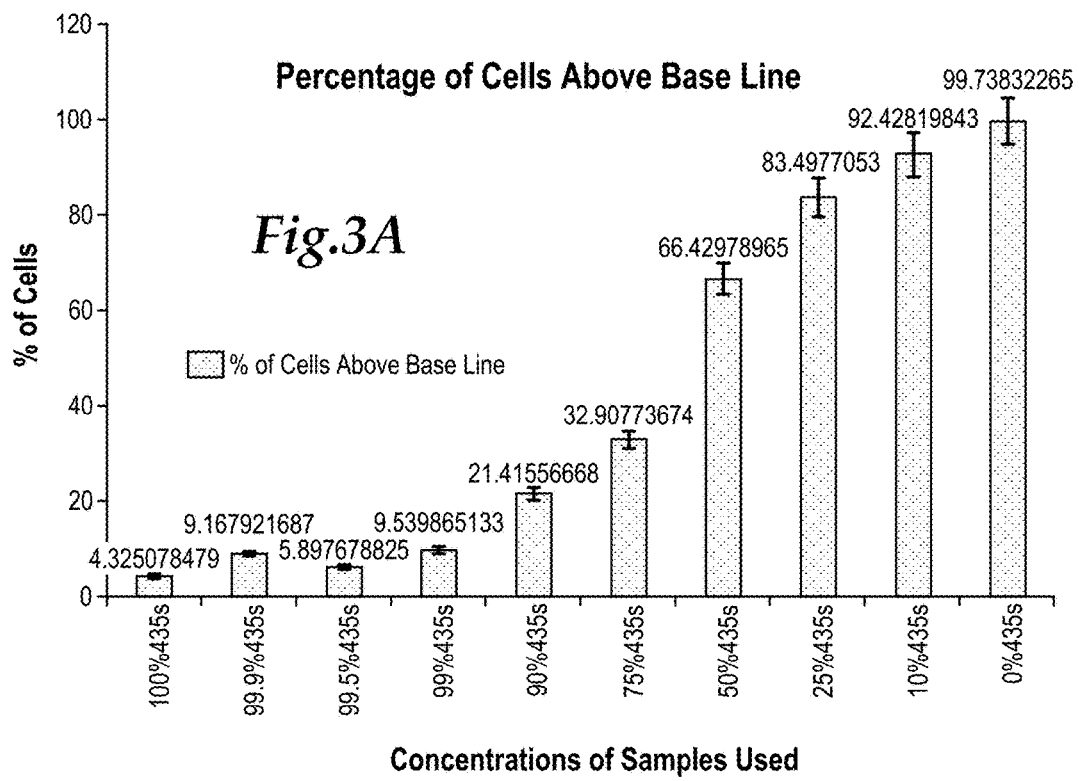
FIG. 3 Bar graph of the percentage of cells with intensity lying 2 standard deviations above the mean EGFR intensity for the 100% MDACC cells (left). Average measured nuclear area as a function of increasing concentration of MDACC 468 cells into the MDACC 435 population.
Figure 3B:
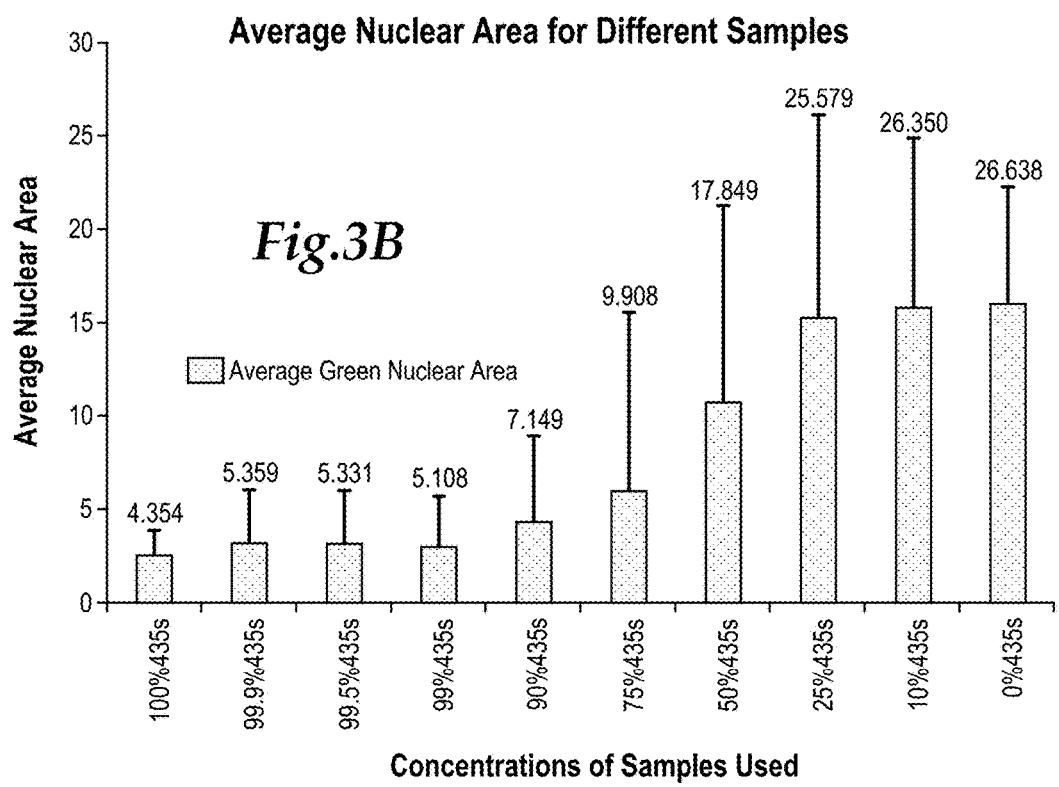

The graphs in FIG. 3 show that as the concentration of the MDACC 468 increase in the mixture of MDACC 435/MDACC 468 from 0, 0.1, 0.5, 1, 10, 25, 50, 75, 90 to 100%, there are noticeable changes in the average intensity per cell with a sharp increase of cells above the mean intensity of EGFR for MDACC 435 cells. This change can also be seen when monitoring the nuclear area as a function of increasing concentration in MDACC 468 cancerous cells.

Figure 4:
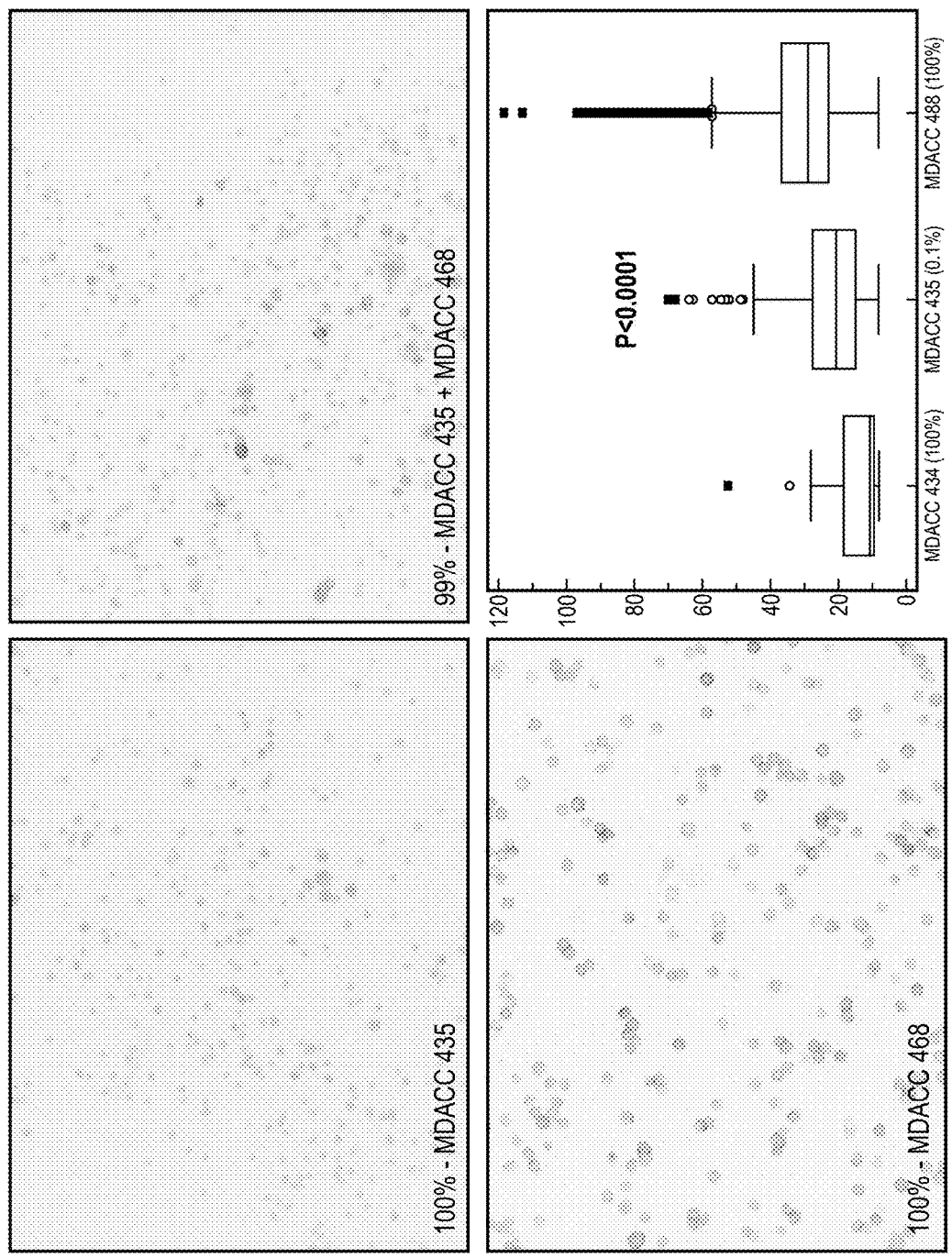
FIG. 4 Microphotographs obtained for 100% MDACC 435 (top left), 99.9% MDACC 435+0.1% MDACC 468 (top right), and 100% MDACC 468 (bottom left). Box and whisker plots of the population of outliers show discrimination with statistical significance between the 100% MDACC 435, and the 99.9% MDACC 435+0.1% MDACC 468 populations. Moreover, the sensitivity of this technique can be seen as we identify and plot the characteristics of the outlier cells for the 100% MDACC 435, and 99.9% MDACC 435+0.1% MDACC 468 populations.

Shown in FIG. 4 are one of the 25-scan microphotographs of the 100% MDACC 435 cells (top left), with the 99.9% MDACC 435+0.1% MDACC 468 (top right). The 100% MDACC 468 cells are shown in the bottom left panel. A Box and whisker plot of the population of outliers from these 3 populations (cells with intensity greater than 2 times the standard deviation of the mean intensity for EGFR in the 100% MDACC 435 cell population) is shown on the bottom right panel, demonstrating the ability of this approach to discriminate between two cell lines with high statistical significance, even when the frequency of one cell line is only about 1 in one thousand. This proof of concept indicates that the sensitivity, already helpful to detect important classes of rare cells, might be pushed down lower. Further dilutions of one cell population into another will be investigated as well as the addition of one extra step of rare cell concentration using magnetic beads and or microfluidic concepts.

Figure 5:
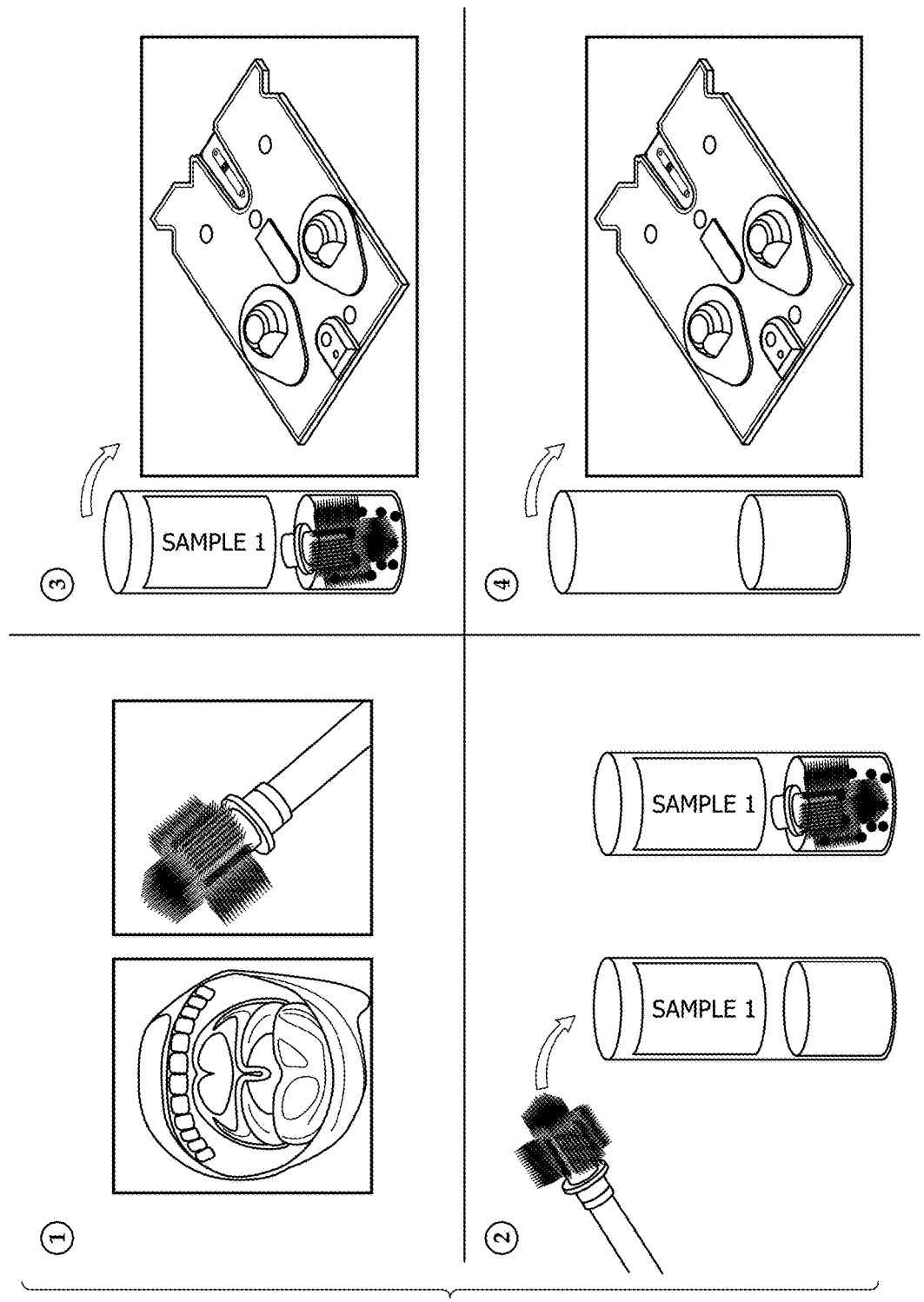
FIG. 5. 1. Cells are collected from a lesion using a brush. 2. Cells are introduced in buffer by snapping head of brush and dropping it into the tube. 3. Cells are introduced into the biochip. 4. A reagent cocktail (if not in dried form inside the biochip) is introduced into the biochip to stain the cells.
Figure 6:
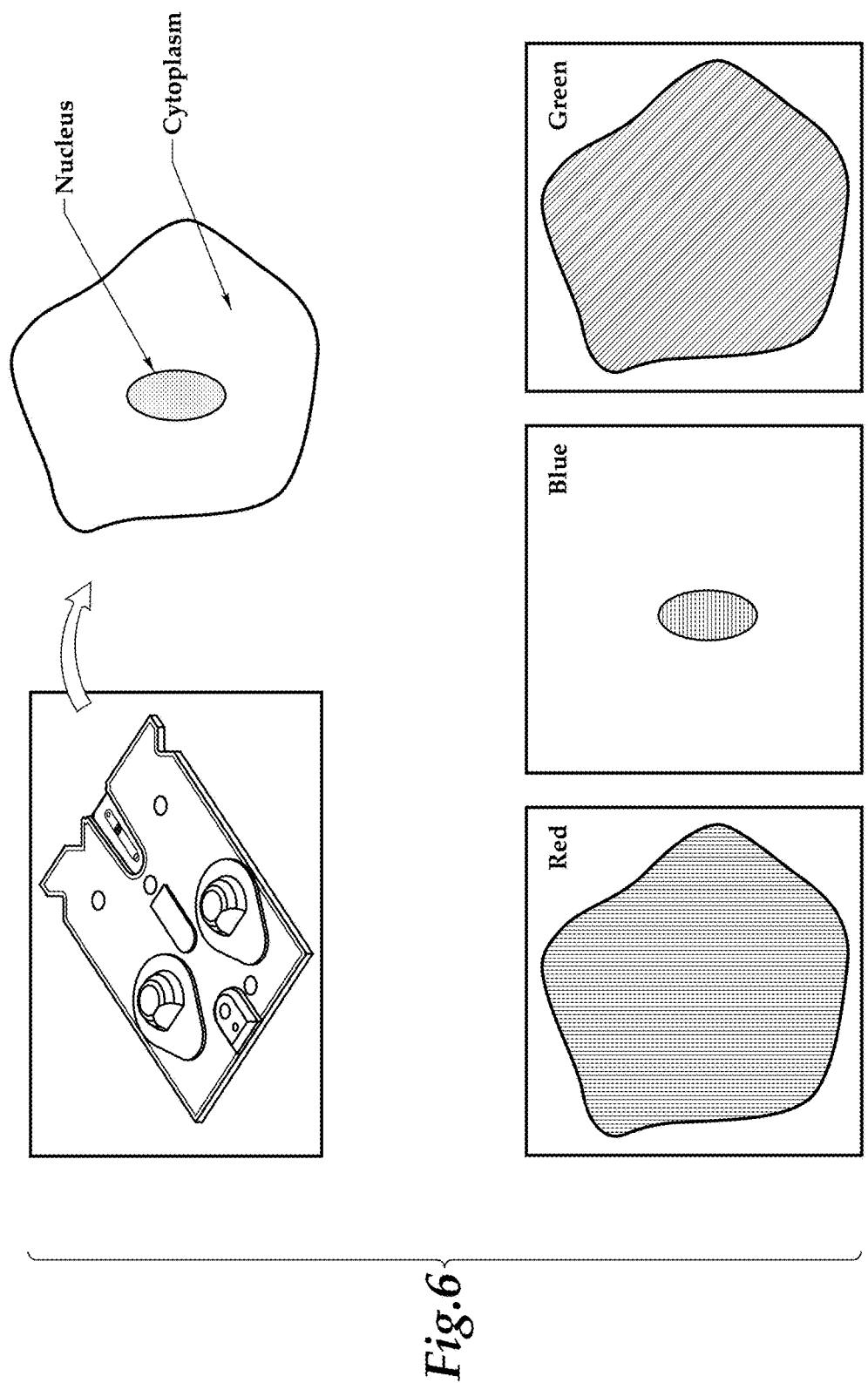
FIG. 6. Cells collected are captured on the membrane surface and labeled by reagents. The cells are identified based on staining of the nucleus with a nuclear dye (in blue channel-solid color), and staining of the cytoplasm with an actin filament stain (in red channel-hatched lines). An antibody to a specific biomarker present either on the surface or in the interior of the cell is labeled in the green channel (dotted).
Figure 7:
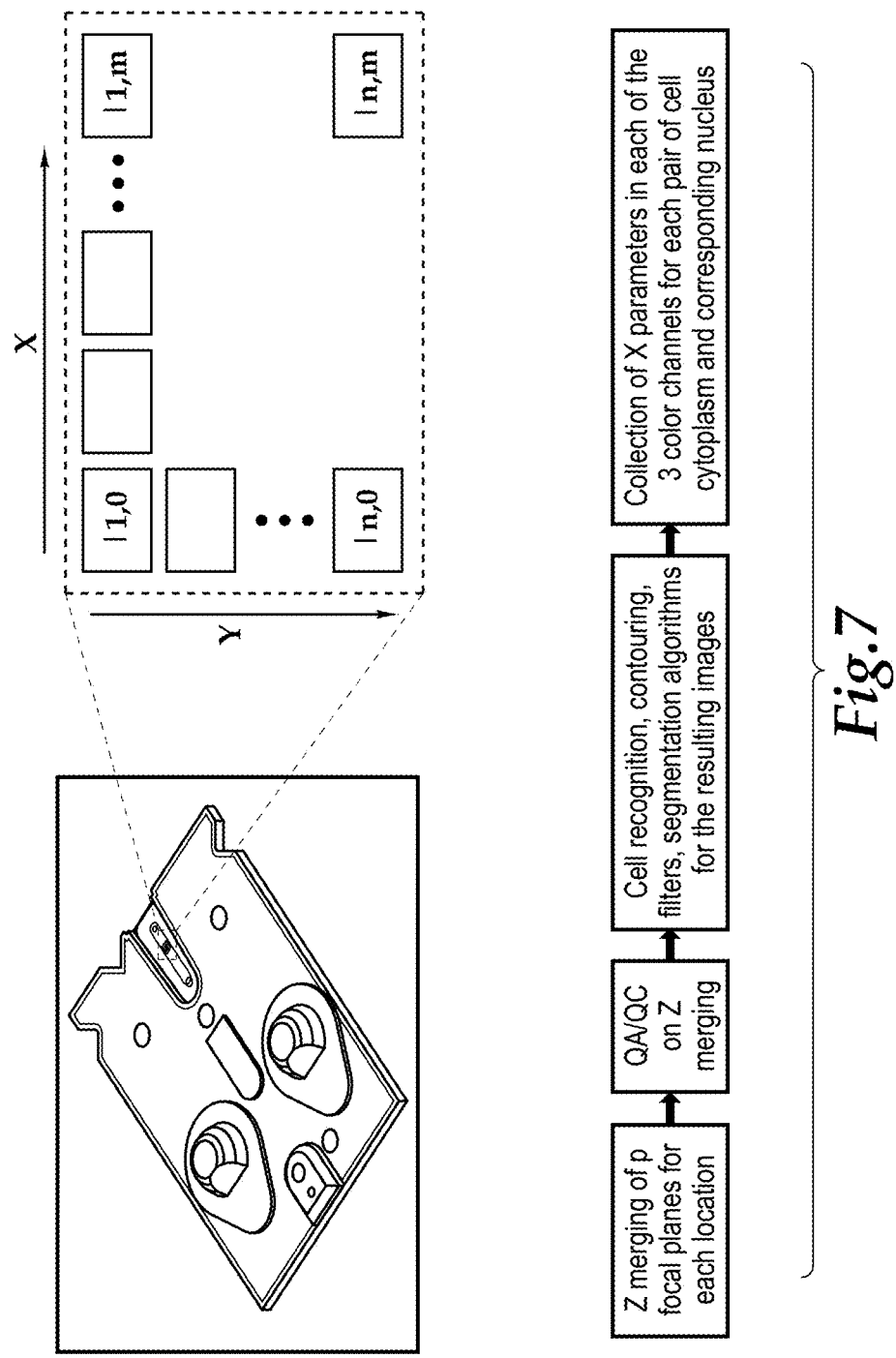
FIG. 7. Schematic showing image processing. For each image, an X-Y scan of the membrane area (variable area), collecting (n×m) non overlapping images at p different focal planes, is acquired. Currently n=m=5, p=3 for 5×5 XY scan with 3 Z-focal planes. Each dataset comprised all acquired images is subjected to a one-push of a button automated routine that does.

The test is run per FIG. 5, and the image analysis proceed as described in FIG. 6-8. Preliminary data for one marker EMMPRIN (CD147) is shown in FIG. 9 (a box and whisker plot that shows a statistical summary of the data wherein the box represents data in the 25-75 percentile, and the line in the box is the median, the lines on each side of the box (hatched line) delineate 10-90% data, and the rest are outliers). Difference between means were statistically significant ($p<0.0001$).

The following references are incorporated by reference in their entirety.

Weigum, S. E.; Floriano, P. N.; Christodoulides, N.; McDevitt, J. T. Lab on a Chip 2007, 7, 995-1003.

Weigum, S. E.; Floriano, P. N.; Redding, S. W.; Yeh, C. K.; Westbrook, S. D.; McGuff, H. S.; Lin, A.; Miller, F. R.; Villarreal, F.; Rowan, S. D.; Vigneswaran, N.; Williams, M. D.; McDevitt, J. T. Cancer Prevention Research 2010, 3, 518-528.

US2008038738

61/413,107, 61/484,492, 61/558,165

WO2007002480, WO2005083423, WO2004009840, WO2005085796, US2009215072 et seq.

What is claimed is:

1. A method of point of care testing to distinguishing oral cancer from dysplasia and benign lesions, said method comprising:
    a) collecting an oral sample from a patient during a patient visit using a rotating brush;
    b) applying said sample to a portable device comprising microfluidics, a power source, display means, a removable and disposable chip comprising reagents for detecting DNA, cytoplasm, and at least three biomarkers selected from the group consisting of AVB6, EGFR, Ki67, Geminin, MCM2, Beta Catenin, and EMMPRIN;
    c) measuring, by using said portable device, nuclear/cytoplasm ratio, cell roundness, cell aspect ratio, and cell shape, and said at least three biomarkers in said sample;
    d) computing, by using said portable device, the risk of oral squamous cell carcinoma (OSCC score) based on said measurements and the formula:

$$\text{OSCC score} = a_0 + a_1 \times P_1 + a_2 \times P_2 + \ldots + a_n \times P_n$$

wherein $a_{1 \to n}$ are weighing coefficients, and $P_{1 \to n}$ are parameters selected from said measurements in step c) and said detecting results from step b), and wherein risk of oral cancer is directly proportional to nuclear/cytoplasmic area ratio, cell roundness, EGFR, KI67, Geminin, AVB6, MCM2, beta catenin and EMMPRIN and inversely correlated with cell aspect ratio and the risk of benign lesions is the reverse; and
    e) communicating, by using said portable device, said risk to the patient in the same patient visit as said collecting step a) to distinguish oral cancer from dysplasia and benign lesions.

2. The method of claim 1, wherein said testing has at least 90% specificity and 90% sensitivity.

3. The method of claim 1, wherein said testing has at least 93% specificity and 97% sensitivity.

* * * * *